US010540067B2

(12) United States Patent
Lindström et al.

(10) Patent No.: US 10,540,067 B2
(45) Date of Patent: *Jan. 21, 2020

(54) BREATHING APPARATUS HAVING A DISPLAY WITH USER SELECTABLE BACKGROUND

(71) Applicant: MAQUET CRITICAL CARE AB, Solna (SE)

(72) Inventors: Madlene Lindström, Farsta (SE); Anette Sunna, Kalmar (SE); Helena Stone, Bromma (SE)

(73) Assignee: MAQUET CRITICAL CARE AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/376,654

(22) Filed: Apr. 5, 2019

(65) Prior Publication Data

US 2019/0227685 A1    Jul. 25, 2019

Related U.S. Application Data

(63) Continuation of application No. 14/409,737, filed as application No. PCT/EP2012/061901 on Jun. 20, 2012, now Pat. No. 10,296,181.

(51) Int. Cl.
*G06F 3/0484* (2013.01)
*A61M 16/00* (2006.01)
(Continued)

(52) U.S. Cl.
CPC ....... *G06F 3/0484* (2013.01); *A61M 16/0051* (2013.01); *A61M 16/021* (2017.08);
(Continued)

(58) Field of Classification Search
CPC ............. G06F 3/0484; A61M 16/0051; A61M 2205/52; A61M 2230/42; A61M 2240/00;
(Continued)

(56) References Cited

U.S. PATENT DOCUMENTS 6,527,700 B1 *  3/2003  Manico .................... A61B 5/16
                                                    600/26
7,225,809 B1 *  6/2007  Bowen ................ A61M 16/024
                                                    128/204.21
(Continued)

FOREIGN PATENT DOCUMENTS

CN         1474992 A     2/2004
CN       101083126 A    12/2007
(Continued)

OTHER PUBLICATIONS

International Search Report and Written Opinion issued in counterpart International Application No. PCT/EP2012/061901, dated Feb. 19, 2013.

(Continued)

*Primary Examiner* — Shourjo Dasgupta
(74) *Attorney, Agent, or Firm* — Wesley Scott Ashton

(57) ABSTRACT

A breathing apparatus and system include a breathing apparatus having a display, an internal memory unit, and a processing unit, and optionally an interface for connecting at least an external memory unit to the apparatus; optionally an external memory unit connectable to the breathing apparatus via the interface; wherein the processing unit is in operative communication with the display, the internal memory unit, and/or the external memory unit when connected to the apparatus via the interface, and the processing unit is configured to provide on at least a portion of the display, a user selectable background stored on at least one of the internal and/or external memory unit, such as a background image, or a background color different than a factory default background color that is not selectable by a user.

20 Claims, 10 Drawing Sheets

(51) Int. Cl.
  *G06F 3/0482* (2013.01)
  *G06F 3/0488* (2013.01)
(52) U.S. Cl.
  CPC .......... *G06F 3/0482* (2013.01); *G06F 3/0488* (2013.01); *G06F 3/04842* (2013.01); *A61M 2205/18* (2013.01); *A61M 2205/3553* (2013.01); *A61M 2205/3584* (2013.01); *A61M 2205/505* (2013.01); *A61M 2205/52* (2013.01); *A61M 2205/583* (2013.01); *A61M 2230/42* (2013.01); *A61M 2240/00* (2013.01)
(58) Field of Classification Search
  CPC ........ A61M 2205/18; A61M 2205/583; A61M 2205/3584
  See application file for complete search history.

(56) References Cited

U.S. PATENT DOCUMENTS

| | | | |
|---|---|---|---|
| 8,527,038 B2 | 9/2013 | Moon | A61B 5/0002 600/513 |
| 8,555,882 B2 | 10/2013 | Wallace et al. | |
| 2001/0027791 A1 | 10/2001 | Wallace et al. | |
| 2002/0133061 A1* | 9/2002 | Manetta | A61M 16/021 600/300 |
| 2005/0010254 A1 | 1/2005 | Zhang | A61B 5/0031 607/9 |
| 2007/0050715 A1 | 3/2007 | Behar | A61B 5/0002 715/706 |
| 2007/0292831 A1 | 12/2007 | Lee | |
| 2008/0072896 A1 | 3/2008 | Setzer et al. | |
| 2008/0204809 A1 | 8/2008 | Miyashita | G06F 17/243 358/1.18 |
| 2009/0024008 A1* | 1/2009 | Brunner | A61M 16/021 600/301 |
| 2009/0144157 A1 | 6/2009 | Saracino | G06Q 30/0277 705/14.73 |
| 2009/0150831 A1 | 6/2009 | Young | G06Q 50/22 715/845 |
| 2009/0216132 A1 | 8/2009 | Orbach | A61B 5/021 600/485 |
| 2010/0030578 A1 | 2/2010 | Siddique | G06Q 10/0637 705/3 |
| 2010/0071696 A1 | 3/2010 | Jafari | A61B 5/021 128/204.23 |
| 2010/0078026 A1 | 4/2010 | Andrieux | A61M 18/024 128/204.21 |
| 2010/0163035 A1* | 7/2010 | Hyde | A61B 5/0484 128/203.14 |
| 2010/0163037 A1* | 7/2010 | Hyde | G06F 19/3462 128/203.14 |
| 2010/0218766 A1 | 9/2010 | Milne | A61M 16/0051 128/204.23 |
| 2010/0275920 A1 | 11/2010 | Tham | A61M 16/0051 128/204.23 |
| 2011/0120469 A1 | 5/2011 | Almagro Frutos | A61M 16/0051 128/204.23 |
| 2011/0167382 A1 | 7/2011 | van Os | |
| 2011/0249006 A1* | 10/2011 | Wallace | A61M 16/0051 345/440 |
| 2011/0259333 A1 | 10/2011 | Sanchez | A61M 16/0051 128/204.23 |
| 2011/0265024 A1 | 10/2011 | Leone | A61M 16/0051 715/771 |
| 2011/0301477 A1 | 12/2011 | Hughes | A61B 5/0205 600/500 |
| 2012/0123219 A1 | 5/2012 | Georgiev et al. | |
| 2012/0180793 A1* | 7/2012 | Schoepke | A61M 16/01 128/204.22 |
| 2012/0185792 A1 | 7/2012 | Kimm | A61B 5/085 715/772 |
| 2012/0192867 A1 | 8/2012 | Lewis | A61M 16/0051 128/204.21 |
| 2012/0313962 A1 | 12/2012 | Hsu | G06F 3/04817 345/593 |
| 2013/0055134 A1 | 2/2013 | Knor | A61M 16/0051 715/771 |
| 2013/0112202 A1 | 5/2013 | Fogelbrink | A61M 16/0057 128/204.21 |
| 2013/0157571 A1 | 6/2013 | Wondka | H04W 52/0245 455/41.2 |
| 2014/0200432 A1 | 7/2014 | Banerji | A61B 5/0488 600/383 |

FOREIGN PATENT DOCUMENTS

| | | | | |
|---|---|---|---|---|
| CN | 101192129 A | | 6/2008 | |
| JP | 2001521416 A | | 11/2001 | |
| JP | 2009195290 | * | 9/2009 | |
| JP | 2009195290 A | | 9/2009 | |
| WO | 9841271 A1 | | 9/1998 | |
| WO | 0239366 A1 | | 5/2002 | |
| WO | 2012029034 A1 | | 3/2012 | |
| WO | WO 2012027643 A2 | | 3/2012 | .......... G06K 9/3266 |

OTHER PUBLICATIONS

International Preliminary Report on Patentability issued in counterpart International Application No. PCT/EP2012/061901, completed Oct. 28, 2014.
Office Action issued in counterpart CN Application No. 201280074089. 5, dated Feb. 3, 2016.
Office Action issued in counterpart JP Application No. 2015-517617, dated Apr. 8, 2016.
Office Action issued in counterpart JP Application No. 2015-517617, dated Aug. 8, 2016.
Office Action issued in countetpart CN Application No. 201280074089. 5, dated Aug. 31, 2018.
Office Action issued in counterpart CN Application No. 201280074089. 5, dated Mar. 8, 2017.
Office Action issued in counterpart EP Application No. 12731364.1, dated Jan. 23, 2018.
"Introduction to Mechanical Ventilation", published on Aug. 15, 2003 to https://www.alc.cuhk.edu.hk/web8/mech%20vent%20intro. htm, retrieved Mar. 5, 2018.
Office Action issued in European Application No. 12731364.1 dated Sep. 3, 2019.

* cited by examiner

A

B

C

BREATHING APPARATUS HAVING A DISPLAY WITH USER SELECTABLE BACKGROUND

This application is continuation application of U.S. patent application Ser. No. 14/409,737, filed Jan. 8, 2015 (now U.S. Pat. No. 10,29,181 B2), which is the U.S. National Phase Application of International Application No. PCT/EP2012/061901 filed on Jun. 20, 2012. The above-mentioned applications and patent are incorporated herein by reference in their entirety.

BACKGROUND OF THE INVENTION

Field of the Invention

This invention pertains in general to the field of breathing apparatuses. More particularly the invention relates to user interfaces of such breathing apparatuses, in particular graphical user interfaces (GUI's) thereof.

Description of Prior Art

Users of breathing apparatuses comprise commonly two groups of users, namely clinical personnel operating the apparatus, and patients receiving ventilatory care. Another group of users of some breathing apparatuses, however, are also members of the family of ventilated patients, or other persons like visitors of the patients, e.g. in intensive care units. This group of users is herein denominated as secondary users. For instance parents of young children treated in Neonatal Intensive Care Units (NICUs) often are put under physiological and even physical stress by the highly technical environment including numerous medical devices permanently showing a multitude of information including complex graphs, curves, metrics. This information is primarily intended for the clinical user and can thus be difficult to interpret for secondary users, thus leading to the aforementioned stress and unnecessary anxiety, concerns, uneasiness, disquiet, nervousness of the secondary users, which are all undesired conditions that are highly desired to be reduced or eliminated.

Screens of intensive care ventilators display during operation a multitude of data, and graphs related to operation thereof, like monitored parameters. It may for instance be very stressful for parents of neonates under treatment in neonatal care units to be exposed to a screen of an intensive care ventilator during the entire time of their stay.

However, reducing this information is a difficult issue as clinical situations may be entered anytime where it is highly important for the clinical personnel to have immediate access to the clinical operation of the apparatus.

Hence, an improved breathing apparatus would be advantageous, in particular providing for reduced stress of secondary users.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a breathing apparatus, a method, and a computer program, according to the appended patent claims.

In particular in neonatal care units, it is of frequent occurrence that all involved try to create a quiet and harmonic environment as a positive contribution to the care given. For this purpose, for instance walls are painted in various colors, cartoons are drawn on the walls, posters are affixed to walls or furniture, etc. Even more personal elements can be seen, like photographs of the patients. All these efforts are done for the purpose of creating a harmonic and familiar environment. However, the medical devices create often the opposite, as they might be perceived as technocratic complicated, and to a certain degree alarming.

The present disclosure provides for a simplified and more harmonic GUI for secondary users. An immediate return to a clinical expert view is provided, if needed, based on a touch screen implementation. The harmonic GUI comprises, herein called "family view" comprises background images that cover a large portion of the display area. Operational parameters and metrics are displayed in the same family view, but in a limited number compared to clinical expert views. Ventilation continues unchanged during the family view. In this manner, the family view is less stressful than a clinical view that in contrast is only showing metrics, parameter curves, and other clinical details that secondary users do not fully understand. Secondary users may even provide own images as background images loadable into the breathing apparatus via an interface thereof. Clinical operators may immediately return to the clinical expert mode by simply touching the display, if desired.

In the present disclosure different layouts of the graphical user interface (GUI) on the screen of the breathing apparatus are selectable by the operator of the breathing apparatus without changing a ventilation mode of a patient connected to the breathing apparatus.

The different layouts may be described as different views. Different views for an identical ventilation mode may be chosen by the operator. The operator may decide which view to choose in dependence of current clinical needs, or treatment situations.

Different views comprise different sets of displayed data elements, such as curves, graphs, metrics, menus etc. related to clinical operation of the breathing apparatus. The curves, graphs, metrics are generally related to operational parameters of the breathing apparatus. Operational parameters include for instance, but are not limited to, current ventilation mode, inspiratory Oxygen concentration, inspiratory pressure, expiratory pressure, inspiratory flow, expiratory flow, Positive End Expiratory Pressure (PEEP), minute volume, tidal volume, breathing cycle, inspiratory to expiratory (I:E) ratio, exhaled carbon dioxide concentration, etc.

Different views may in addition or alternatively differ in the background of the GUI. A background may be a different solid color. A background may be an image of non-solid color, preferably a photographic image reproduced on the GUI.

One such view is disclosed as the "family view". The layout of the GUI of the family view is a harmonic and lean in contrast to a full operational mode comprising a larger amount of displayed data elements. The family view comprises a background image in combination with a limited set of displayed data elements. The data elements may comprise a number of metrics of operational parameters, wherein the number is preferably kept to a minimum.

The background image may be animated. Alternatively, or in addition, the background image may be a still image, combined with an overlay animation displayed on the GUI. The animation is provided as a simulation of currently ongoing ventilation of a patient connected to the breathing apparatus. The animation may be provided in form of bubbles floating over the screen. Alternatively, or in addition, the animation may be provided in form of a light wave travelling over the screen. Alternatively, or in addition, the animation may be provided in form of a miniature graph showing a time curve of an operational parameter, such as inspiratory or expiratory pressure or flow.

The layout may be user adapted. A suitable background image may be chosen from a number of default backgrounds stored in an internal memory of the breathing apparatus. Users may provide their own images for display on the screen of the breathing apparatus. These user supplied images may be provided via a communication interface of the apparatus. This interface may be a wired interface, like USB allowing connection of USB memory units having the image(s) stored thereon. Alternatively, or in addition, the communication interface may be wireless, and/or network based. The image(s) may be accesses or downloaded from an external memory. The image(s) may be downloaded into an internal memory of the apparatus before being displayed. In this manner, the external memory unit can be disconnected after download of the image(s). A plurality of images may be provided for displaying a changing background in a view, by successive display of different images as background, from a plurality of images, such as a slideshow.

Alternatively, or in addition, a sound may be played in a certain view, such as the family view. The sound may be played via a loudspeaker in the breathing apparatus or connected thereto. The sound may be music. The sound may be user adapted, i.e. provided by a user of the apparatus, like a secondary user.

The disclosed family view contributes to a harmonic environment at intensive care units. Stress is reduced for patients and family present at the breathing apparatus.

According to one aspect of the disclosure, a breathing apparatus system is provided. The breathing apparatus system includes a breathing apparatus having a display, an internal memory unit, and a processing unit. The apparatus may have an interface for connecting at least an external memory unit to the apparatus. The breathing apparatus system may include an external memory unit connectable to the breathing apparatus via the interface. The processing unit is in operative communication with the display, the internal memory unit, and/or the external memory unit when connected to the apparatus via the interface, and the processing unit is configured to provide on at least a portion of the display, a user selectable background stored on at least one of the internal and/or external memory unit, such as a background image, or a background color different than a factory default background color that is not selectable by a user.

According to another aspect of the disclosure, a method is provided. The method is a method of internally controlling a display of a breathing apparatus. The method includes providing a user selectable background for displaying on at least a portion of the display, such as a background image, or a background color different than a factory default background color that is not selectable by a user. The background image is either selectable from at least one default image stored on an internal memory unit of the breathing apparatus, or from an external memory unit connectable to the breathing apparatus.

According to a further aspect of the disclosure, a non-transitory computer-readable storage medium encoded with programming instructions, the storage medium being loaded into a computerized control system of a breathing apparatus is provided, the programming instructions causing the computerized control unit to control display unit of the breathing apparatus during operation by providing a user selectable background for displaying on at least a portion of the display, such as a background image, or a background color different than a factory default background color that is not selectable by a user, wherein the background image is either selectable from at least one default image stored on an internal memory unit of the breathing apparatus, or from an external memory unit connectable to the breathing apparatus, and preferably switching between a plurality of operational modes of the apparatus, the operational modes including a first operational mode in which a first number of operational parameters is displayed on the display without the image as the background, and an alternative second operational mode in which a second number of operational parameters, preferably less than the first number, are displayed on the display and the background image is displayed as a background image on the display.

These operational modes in the present context of the disclosure, and particular examples thereof, are referring to different views of a Graphical User interface of a breathing apparatus. The operational modes should hence not be confused with breathing modes of the breathing apparatus, for which some examples will be given below in the detailed description.

Further embodiments of the disclosure are defined in the dependent claims, wherein features for the second and subsequent aspects of the disclosure are as for the first aspect mutatis mutandis.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF THE PREFERRED EMBODIMENTS

Figure 1:
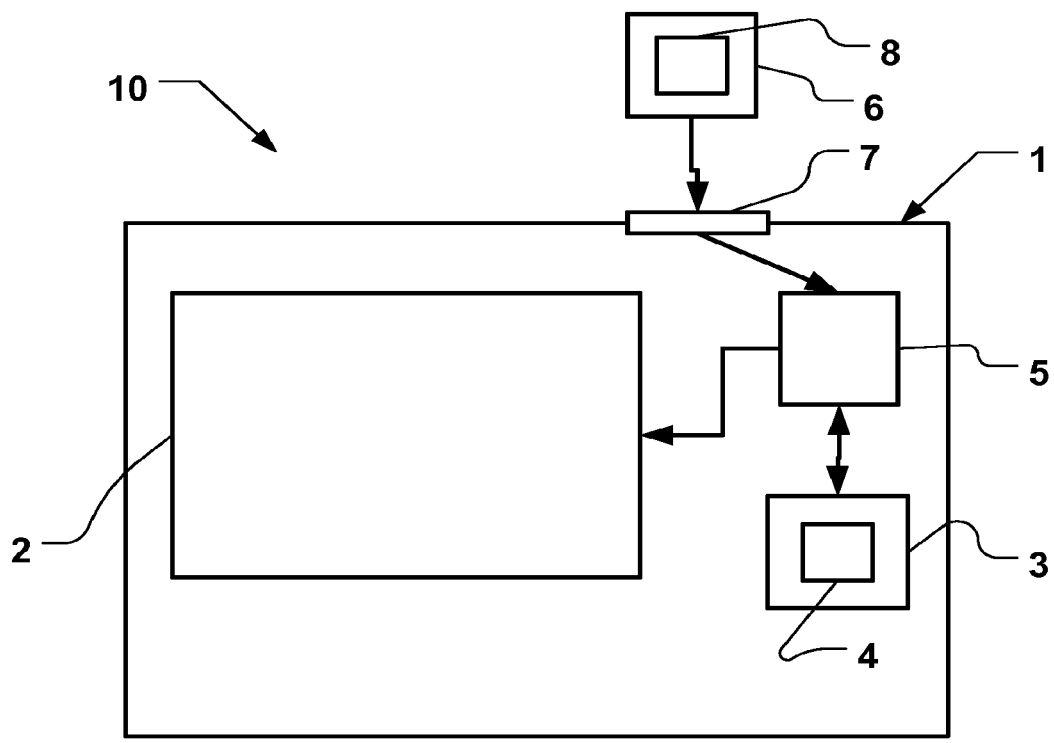
FIG. 1 is a schematic illustration of breathing apparatus system.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Examples of simplified and harmonic family views for secondary users will now be described. Each "family view" comprises background images that cover a large portion of the display area. Operational parameters and metrics are also displayed in the same family view, in the foreground, i.e. in front of a background image, but in a limited number compared to clinical expert views. Ventilation continues as mentioned during the family view. In this manner, the family view is less stressful than a clinical view that in contrast is only showing metrics, parameter curves, and other clinical details that secondary users do not fully understand. Secondary users may even provide own images as background images loadable into the breathing apparatus via an interface thereof. Clinical operators may adjust selected operational parameters displayed in the family view, without leaving it. Clinical operators may also handle alarms in the family view, without leaving it. However, clinical operators may immediately return to the clinical expert mode by simply touching the display, if desired.

Figure 13:
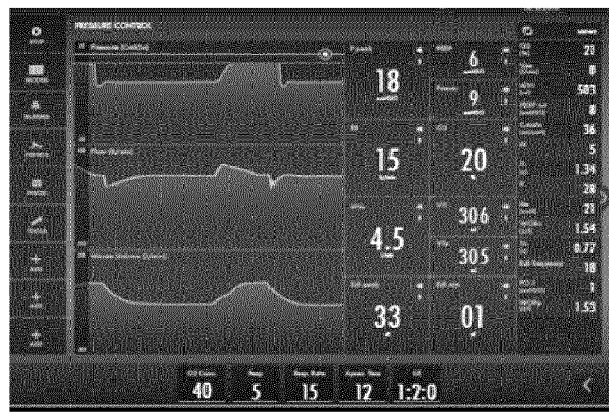
Figure 13:
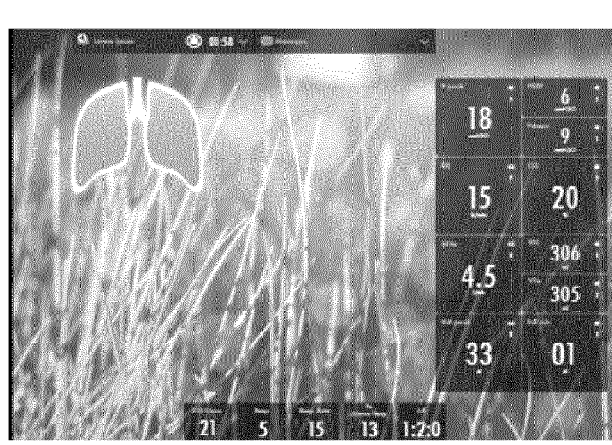
Figure 13:

The difference between different operational modes (views) is illustrated in FIG. 13.

Section A of FIG. 13 shows a clinical expert mode view 24 with various metrics, parameter curves, menus, etc. This is an example of a very sophisticated view, which is very useful for clinical operators of a breathing apparatus, but may be stressful to secondary users. The number of metric and/or curves as well as the graphical layout may be varied, for instance in different clinical views. The illustrated expert mode view 24 may be an advanced view. A less advanced view may show a reduced number of metrics and/or curves than the illustrated expert mode view 24. This less advanced kind of clinical view may be called "basic view". Curves may be replaced by loops in certain views. Clinical views are intended for clinical operators of a breathing apparatus.

Section B of FIG. 13, shows an example of a family view 22. The family view includes a reduced, or minimized, number of metrics. It can be seen in the illustration that this family view 22 comprises less clinical information elements, and a background image. The background image is exclusively visible on a large portion of the display area as there are no foreground objects. The image is not related to clinical information and thus a de-association from the clinical environment may be obtained. Secondary users are less stressed by the GUI of a family view. As can be seen, the metrics and a field for adjustment of operational parameters is of a similar size as in the clinical expert view 24. Hence, a family view should not be confused with the kind of view shown in Section C of FIG. 13, namely a so called "distance view" 25.

The distance view 25 includes a reduced number of displayed metrics (compared to expert view 24) and/or curves that are graphically enlarged so that they can be read from a larger distance, compared to other views like those of the expert view 24 or family view 22. It should be noted that the distance view 25 is also a clinical view intended for the clinical operator of the breathing apparatus.

The following description describes embodiments applicable to a breathing apparatus. The detailed description will initially describe the different operational modes of the GUI for one and the same ventilation mode. Following sections describe specific examples of views with reference to the Figures.

Herein are different operational modes of breathing apparatuses discussed. Preferably, these operational modes are in the present context of the disclosure, and particular examples thereof, referring to different views of a GUI of a breathing apparatus. Different views include views of the GUI during operation of the breathing apparatus. In particular, different views are disclosed for identical breathing modes of the breathing apparatus, i.e. ventilation modes of a patient having its airways connected to a pneumatic part of the breathing apparatus. Breathing modes are for instance Pressure Controlled ventilation (PCV), Volume Controlled ventilation (VCV), Pressure Support Ventilation (PSV), Synchronized Intermittent Mandatory Ventilation (SIMV), CPAP (continuous positive airway pressure ventilation (CPAP), etc. Different operational modes are for instance an expert ventilation view 24 and a family view 22 for a breathing mode, such as PCV. The operational modes, or views, differ depending on clinical situations where the views are particularly advantageous over other views.

For instance a second mode has a more limited number of metric than a first mode. This will now be elucidated in more detail.

Now turning to the figures, a breathing apparatus system 10 is described with initial reference to FIG. 1.

The system 10 includes a breathing apparatus 1. The breathing apparatus 1 has a display 2, an internal memory unit 3, and a processing unit 5.

The internal memory unit 3 is provided to have data elements 4 stored thereon. The data elements 4 may be background color data, background image data, sound data, multimedia data, etc. The data elements 4 are different from data elements for a background color stored on a memory of the apparatus 1, which are stored during manufacturing as a factory default background color that is not selectable by a user of the apparatus 1.

The apparatus 1 may have a plurality of operational modes (views), wherein the background and number of metrics and/or time curves of the operational parameters on the display is different in different operational modes.

Alternatively, or in addition, the background is different for different patient categories, such as adult, pediatric, neonatal; and/or type of product. Type of product is referring to the breathing apparatus, and includes for instance product types such as intensive care ventilators, home care ventilators, anesthesia machines, etc. A type of product may in particular refer to a specific hardware product dedicated for ventilation of a specific patient group, like neonates, or adults. Even more particular, some examples may comprise a first operational mode, preferably clinical modes dedicated for clinical personnel and operators of breathing apparatus, where the background color is different for a specific patient group. In this manner, the clinical personnel may quickly identify, even from a distance, that the correct patient group is chosen, or a breathing apparatus for ventilating a correct patient category is operated with a patient that is ventilated or to be ventilated. The background color is in these examples not determinable by a user, but fixed to a background color to be associated with that patient group. Operational safety of such breathing apparatus may thus be improved.

The processing unit 5 is configured to provide a plurality of operational modes of the apparatus. The operational modes include the first operational mode. Here the processing unit 5 may be configured to display a first number of operational parameters on the display 2 with a factory default background color for the first operational mode.

Further, the processing unit 5 is configured to provide an alternative, preferably user selectable, second operational mode in which a second number of operational parameters, preferably less than the first number, are displayed on the display 2 and the processing unit 5 is configured to display the image as a background image on the display behind the displayed operational parameters.

The current operational mode is thus easy to recognize by operators of the apparatus 1.

The display 2 has a total display area. The processing unit 5 is configured to display metrics and/or time curves of operational parameters on the display 2.

The processing unit 5 may be configured to provide a first number of metrics and/or time curves of operational parameters of the breathing apparatus on the display 2 in a first operational mode, and a second number of metrics and/or time curves of the operational parameters on the display in a second operational mode. The second number of metrics and/or time curves of the operational parameters is less than the first number. The second number may also be zero. As explained above, the same identical breathing mode is running during both operational modes (views).

The processing unit 5 may be configured to display metrics and/or time curves of operational parameters on substantially the entire display area in the first operational mode. Preferably no image is shown in the background in the first operational mode.

This first operational mode may in an example be an advanced ventilation mode for clinical full experts like respiratory therapists. This mode is very advantageous during demanding clinical situations or during set-up of a breathing mode for instance. However, secondary users may have issues with a clinical full expert view as explained in the background section above.

The first operational mode may in other examples be a basic ventilation mode, a distance mode with a large display of operational parameters metrics to be readable from a larger distance than an arm's length or bedside environment of the apparatus 1. When returning from the family view to the first operational mode, the apparatus returns preferably to the clinical mode which was active when switching to the family view. Alternatively, the apparatus may return to other clinical modes from the family view. The apparatus may return to a default clinical mode, like the clinical expert mode. Alternatively, the apparatus may return to a basic clinical mode as default, but to a clinical expert mode when an alarm is active in the family view and an operator instructs the apparatus to leave the family view, as described below.

The processing unit 5 may be configured to display the background image only on a display sub-area of the total display area of the display 2 in the second operational mode. In an example, the sub area may be at least 75% of the total display in a second operational mode. In contrast, in the first operational mode a larger portion of the screen area is used for displaying metrics and/or time curves of operational parameters. In more detail, the display 2 has a total display area, wherein said processing unit is configured to display clinical information including a first number of metrics and/or time curves of operational parameters on substantially the entire display area in the first operational mode. In the family view, i.e. the second operational mode, the processing unit is configured to display at least a portion of said background image only on a display sub-area of said entire display area. The background may be shown on substantially the total display. The background image may be shown behind metrics and/or time curves. The background image may be shown opaquely behind the metrics and/or time curves.

In the first operational mode/view, the background in the GUI on the display 2 is preferably not selectable by an operator of the breathing apparatus 1.

In the second operational mode/view, the background in the GUI on the display 2 can be modified and is selectable by an operator of the breathing apparatus 1.

The apparatus 1 may have a communication interface 7 for connecting at least an external memory unit 6 to the apparatus 1.

The breathing apparatus system 10 may include the external memory unit 6 connectable to the breathing apparatus via the interface 7. The external memory unit 6 is provided to have data elements 8 stored thereon. The data elements 8 may be background color data, background image data, sound data, multimedia data, etc.

The processing unit 5 is in operative communication with the display 2, the internal memory unit 3, and/or the external memory unit 6 when connected to the apparatus 1 via the interface 7.

The processing unit 5 is configured to provide on at least a portion of the display 2, a user selectable background stored as data elements 4, 8 on at least one of the internal and/or external memory unit 3, 6.

The internal memory unit 3 may be configured to store data elements 4 for an image. Alternatively, or in addition, the external memory unit 6 is configured to store data elements 8 for an image.

The internal memory unit 3 may have at least one background data element for a default background stored thereon. A default background data element is stored during manufacturing of the apparatus 1 and available for selection by an operator of the apparatus 1. Preferably a plurality of default background data elements is stored for a plurality of different backgrounds. In the latter case, the operator can choose from the plurality of backgrounds to be displayed in a specific view, in particular the family view. When the operator has chosen a specific background based on the default background data elements available, the processing unit 5 loads the corresponding default background data element for displaying on screen 2.

A background data element may comprise data for a still image to be displayed as a background in a view. The processing unit 5 may be configured to display the background image opaquely behind at least a portion of the display where a foreground object, such as operational parameter values, is displayed.

Alternatively, or in addition, the background data element may comprise data for a moving or animated image to be displayed as an animated (not still image) background in a view. This may for instance be image elements like the grass blades shown in some of the Figures moving in a rocking motion, like in a lightly windy environment. Other examples are moving trees, drops spreading on a water surface, walking animals, etc.

Alternatively, or in addition, the background data element comprises data for overlay over a background composed of a still image or an animated image. This may for instance be the below described bubbles, a light pulse, a visual clinical representation like a pair of lungs, a patient chest, etc. Other image elements that are animated may be envisaged, like moving clouds An animated background image and/or an overly animated image portion are shown for illustrating ongoing ventilation and/or breathing pattern of a patient connected to the apparatus. The motion/animation may be controlled by the processor 5 based on an ongoing ventilation. A fixed motion may be turned on when ventilation is ongoing. Alternatively, the animation/motion may be synchronized with the breathing pattern of the ventilated patient. Synchronization may comprise a motion of an image element in one direction during inspiration, and in another direction during expiration. The motion may also be in the same direction during inspiration and expiration. A pause component of a breathing pattern or an end expiratory plateau phase may be illustrated as a slowed down motion or a stopped motion of the image element during this specific phase of the breathing cycle of the ventilated patient.

The motion may be a default motion that is applied to any of the breathing patterns deliverable by the breathing apparatus.

The same motion may be applied to any of the breathing patterns deliverable by the breathing apparatus.

Alternatively, different motions may be provided for different breathing patterns or ventilation modes.

In some examples of the disclosure, the visual clinical representation is not a lung and the animated portion. The visual clinical representation is in some examples synchronized with a breathing pattern of the patient fluidly connected to the apparatus.

Alternatively, or in addition, the motion may be changed in dependence of a specific event or state of an ongoing breathing pattern or ventilation mode. In the latter case, clinical personnel may quickly identify more information than merely an ongoing ventilation. This may in particular be advantageous when the background motion has a sufficient size, i.e. portion of the screen size to be identifiable from a distance larger than usual operational perimeter distance, i.e. within an arm's length of the apparatus. This may also be advantageous as the changed motion may be presented in a way that secondary users do not actually see the information provided to the clinical personnel, as the secondary users are not familiar with the encryption code transposing the clinically relevant information into graphical information of the background motion. For instance the maximum size of bubbles described below may be related to an operational parameter value, such as peak inspiratory pressure.

Alternatively, or in addition, a color code may be applied to the background elements in motion. For instance, a color of bubbles may be changed in dependence of an operational parameter value. A non limiting example is that clinically acceptable values for the ventilated patient are displayed as light bubbles (e.g. white, grey). Values near a threshold to clinically unusual values may lead to a switch of color. A non limiting example is that clinically less acceptable values for the ventilated patient are displayed as yellow bubbles. Values of clinically unusual ranges may lead to a switch of color. A non limiting example is that clinically unusual values for the ventilated patient are displayed as orange or red bubbles. Alternatively, or in addition to a color change, the brightness of background elements in motion may be changed mutatis mutandis.

Alternatively, or in addition, a change of transparency may be applied to the background elements in motion. For instance, a transparency or opaqueness of the below described bubbles may be changed in dependence of an operational parameter value. Values of transparency may change in dependence of clinically acceptable or unusual values of operational parameters as described in the previous paragraph in relation to a color change.

Alternatively, or in addition, to changing the appearance of all background elements in motion, it may also be envisaged that only a portion of the background elements in motion is changed in dependence of the current ventilation. Single elements may be changed, like a single bubble.

Now, a first example of a family view is described with reference to FIGS. 4 and 5. The view 20 is shown on a display 2 during normal operation of a breathing apparatus 1, i.e. a patient ventilated with a certain breathing mode. In the Figures, it can be seen that the breathing mode 300 is pressure control.

A background image 200 is displayed on screen 2. In the example, the background image is a close up view of a meadow with grass blades. The background image is kept in a friendly color tone, here grass green.

On a first display area 30 information data elements related to the current breathing mode 300 are displayed. A miniature curve display element 310 is shown and described in more detail below. Four metric display elements 320, 321, 322, 323 show current values of operational parameters, like peak pressure, I:E ratio, etc. The first display area 30 is illustrated in more detail in FIG. 5. It can be seen that the display elements 320-323 are partly transparent so that the background shines through. The display area 30 and related information data elements take only a minor portion of the entire screen surface of display 2. Thus, secondary users are less focused on the display area 30 and the clinical aspects are experienced less stressful.

Figure 12A:
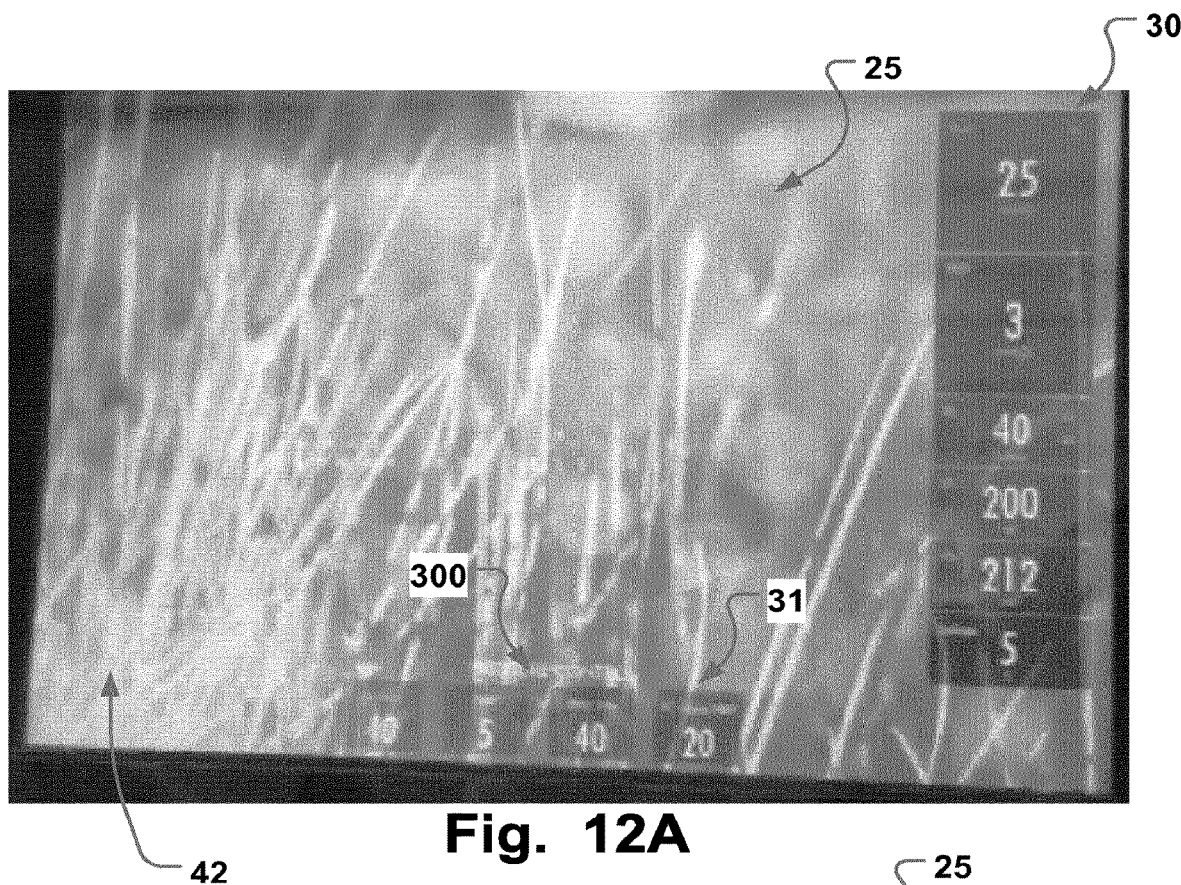
Figure 12B:
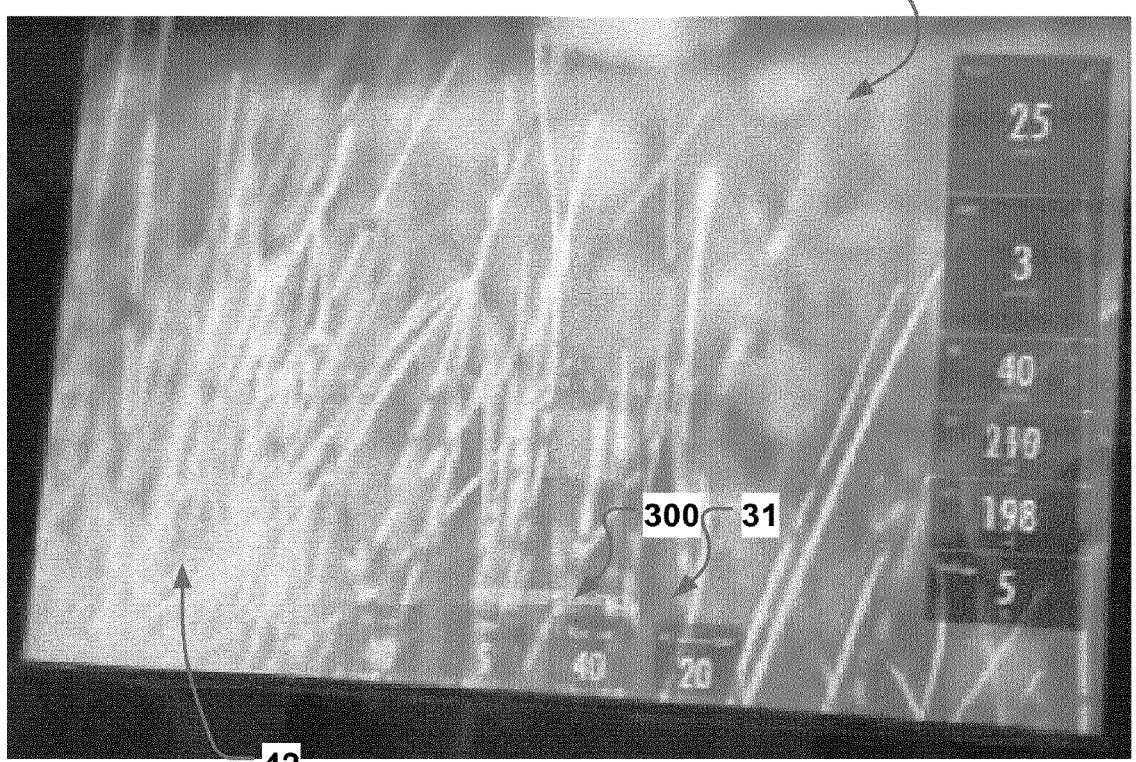

As shown in FIGS. 12A, 12B a view 25 may have the current breathing mode displayed at a lower portion of the display 2. Other positions may be chosen.

A second display area 31 may be provided. In case of display 2 being a touch screen, a tap on the second display area may enter a mode for changing certain operational parameters without leaving the second operational mode.

Displaying one or more operational parameters in area 31 allows for a quick accessibility and possible adjustment of these operational parameters.

The second display area 31 may comprise further displayed operational breathing parameters, such as shown in in FIGS. 12A, 12B. The size of displayed objects may vary. Larger objects, such as in the upper portion of the first region in FIG. 12, B may be used for certain operational parameters, such as more important parameters for certain breathing modes. In this manner, the harmonic, stress-reducing effect of the view is obtained while clinical personnel are presented with sufficient operational parameter values in a weighted manner. Hence, the clinical safety is maintained while less stressful for secondary users.

In case an operator desires to leave the second operational mode, this may be done in a number of ways, as will be explained in detail further below. One way is that the second operational mode is left immediately, preferably to the first operational mode, by an operator touching, e.g. tapping, anywhere on the display 2. Alternatively, an operator may touch the display at one or more defined sub areas of the display dedicated for the purpose of allowing quickly leaving the second operational mode. Alternatively, in addition, the apparatus 1 may leave the second operational mode automatically in certain predefined alarm scenarios.

In the illustrated example, the background of the family view 20 is shown as grass blades 41 in a convenient, friendly green color. The background covers the majority of the display area.

Figure 4:
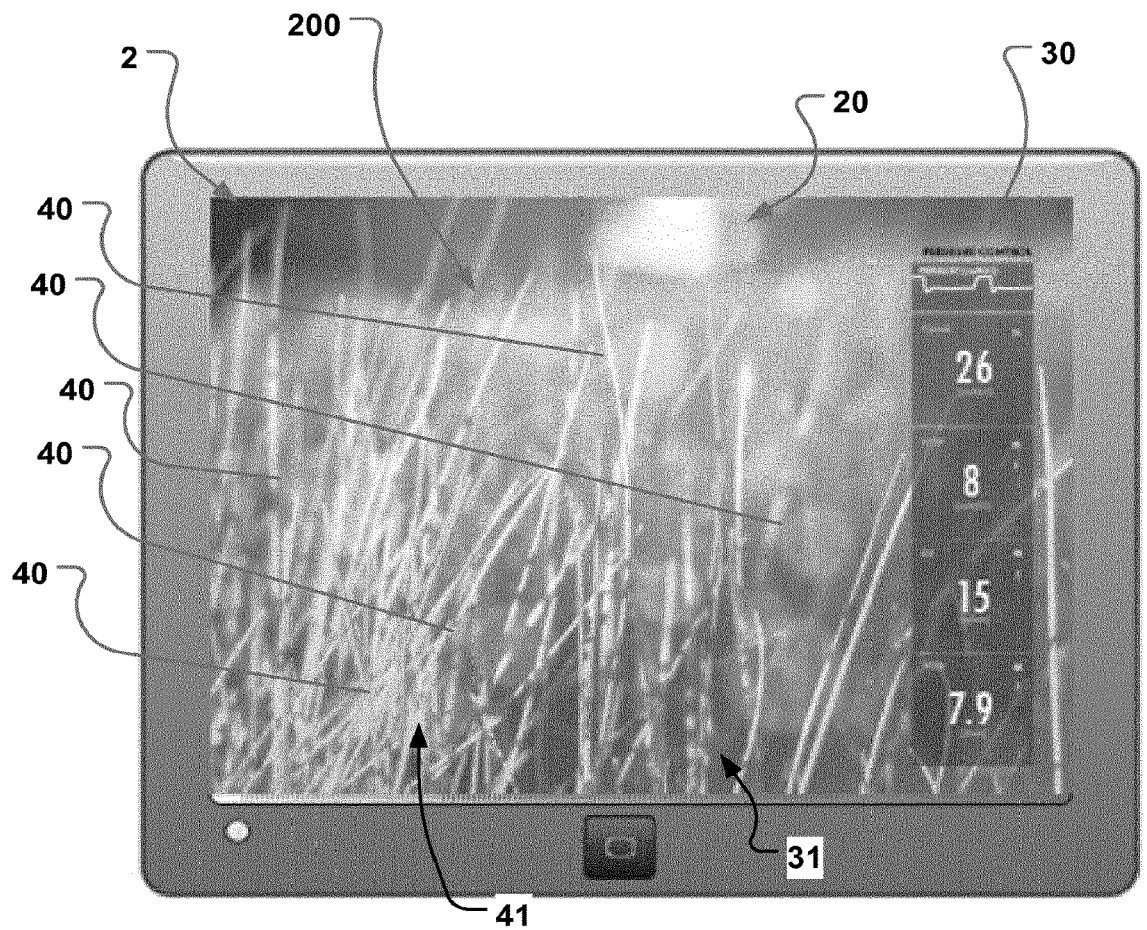
FIGS. 4, 5, 6, 7, 8, 9, 10, 11A, 11B, 11C, 12A, 12B, and 13 are illustrations of examples of views including graphical user interfaces, or parts thereof, of a breathing apparatus.

A plurality of bubbles 20 can be seen in FIG. 4 as an overlay on the background of grass blades. The bubbles are shown in a light tone, partly transparent so that the grass blades can be seen through the bubbles.

Bubbles that float across the screen indicate that ventilation is ongoing. The bubbles may move continuously across the screen without any synchronization with the breathing pattern, be it inspiratory, expiratory, or pause components thereof. This indicates to a user that ventilation of the patient is actually ongoing. The bubbles may still change shape or size while floating across the screen.

Figure 11A:
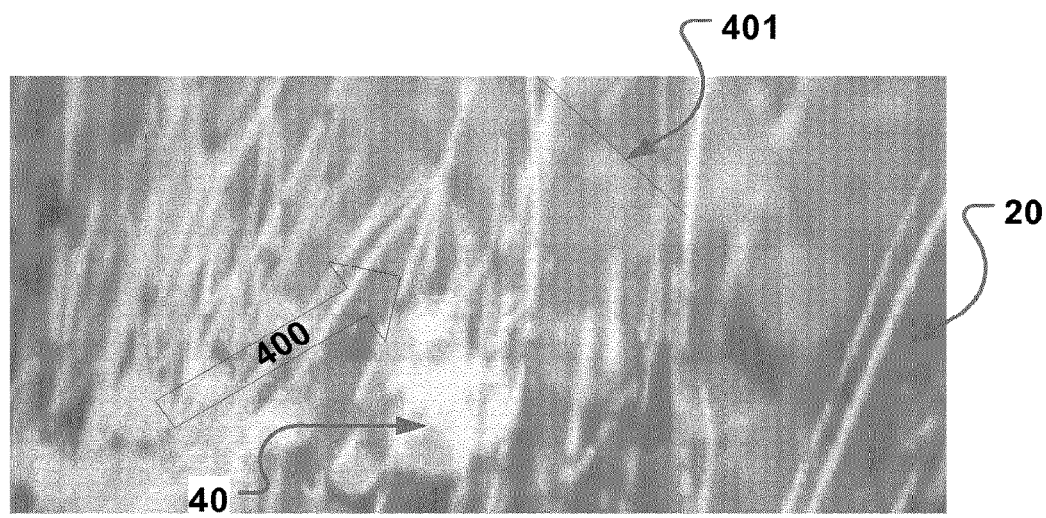
Figure 11B:
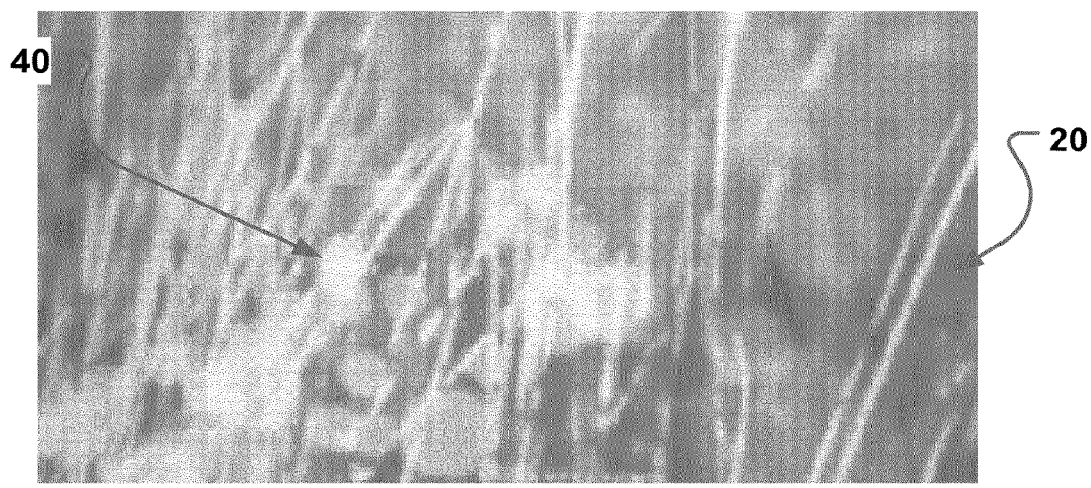
Figure 11C:
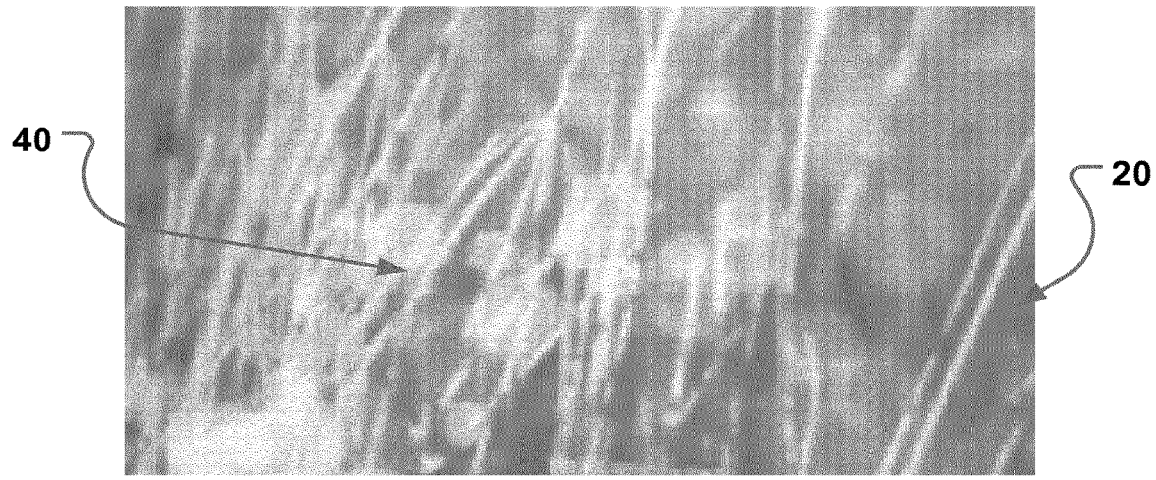

A sequence of moving bubbles is given in FIGS. 11A, 11B and 11C as a non-limiting example of moving background objects. Here, the bubbles 40 float generally in a direction of arrow 400 towards a display area indicated by line 401. The bubbles emerge from the lower left corner of the screen and move along a path towards the line 401. The trajectory of the bubbles is preferably non-straight, preferably sinusoidal, generally along arrow 400. The trajectory of the bubbles is preferably different for each bubble. Bubbles 40 fade out towards the line 401. Along the trajectory, the bubbles change size. In the example, the bubbles repeatedly expand and get smaller along their path.

Alternatively, or in addition to the motion of a background element, such as the bubbles 40, a breathing sound may be produced by the apparatus 1. In this manner, the harmonic environment is supported. The breathing sound may be synchronized with the actual breathing pattern of the ventilated patient.

The sound may be changed to a different sound if an alarm situation arises.

Alternative shapes than bubbles may of course be envisaged by the skilled person having knowledge of the present disclosure.

An example is for instance that the grass blades shown in some of the Figures move, like in a windy environment. A in a rocking motion may be shown by the animated image elements. The rocking motion may be synchronized with a presently ventilated patient's breathing pattern.

Another example is illustrated with reference to FIGS. 12, 12B. A light wave 42 enters the screen. In the example, it enters from the lower left corner of the screen and spreads towards the middle of the screen through the lower left quadrant of the screen. The light wave is an overlay over the background image of the view 25. It may be a cloud like or fog like brighter screen area entering over the background image, which eventually may fade out in a certain screen region, or pass over the entire screen. The light wave in the illustrated example fades out towards the center region of the screen. Again, the light wave may be synchronized with patient breathing patterns (or not).

Animations, or moving elements, such as the bubbles or the light wave animation can be provided in such a scale, or on such a large portion of the screen, that the animations can be seen from a relative large distance. The animations can thus be easily be interpreted from a distance, namely that ventilation is ongoing.

Figure 5:
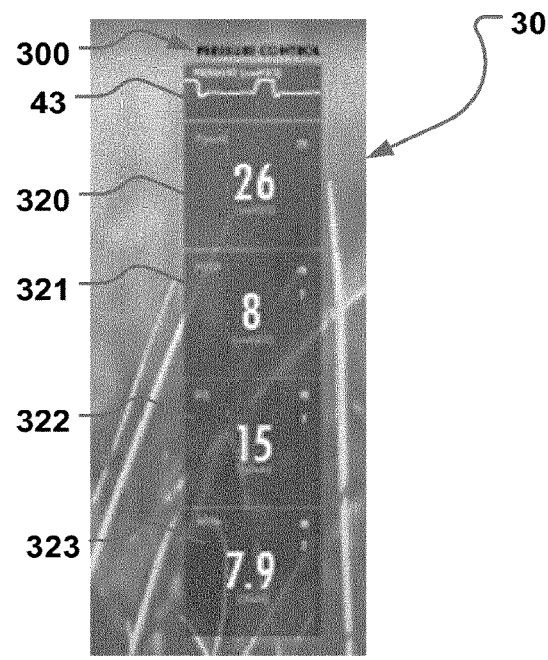

A further example of an animation is shown in FIGS. 4 and 5. Here, a curve of an operational parameter related to the ventilation of the patient is provided. The curve is a miniature curve display element 310. A curve is moving within the window of the display element 310. The curve may for instance be a rolling pressure curve of flow curve illustrating the ventilation of the patient over time.

Hence, several animations may be provided simultaneously, e.g. one for the secondary users and one for the clinical personnel. In this manner both the stress reducing effect is obtained as well as rather detailed clinical information is available without leaving the view 20 for a more detailed view, such as an expert ventilation view of the present breathing mode. This may further reduce to the stress reduction as unnecessary switching or operation of the breathing apparatus 1 may be avoided, depending on the clinical situation.

Each of the animations, such as the described, indicates to the user or operator of the apparatus that it is in operation and a connected patient is ventilated. Alternatively or additionally, the animations may move synchronized with the breathing pattern, be synchronized it inspiratory, expiratory, or pause components thereof.

The processing unit is configured to control the animation to be displayed in examples of the second operational mode when a patient is connected to the breathing apparatus 1 and ventilated by the latter. This in turn means that the animation is not displayed in absence of such ventilation. An absence of an animation with connected patient is thus provided to the operator as an indication of the lack of ventilation of the patient. This is of course accompanied by an alarm indication by the breathing apparatus. However, the operator will with a quick glimpse be able to see the seriousness of the alarm based on the absence of the animation. The operator may then react with suitable measures, like check tubing connections, adapt therapy of the patient, etc. Alternatively, or in addition, the appearance of the animation may provide a information for the seriousness of an alarm situation, such as for instance by the intensity of bubbles, their size, color, transparency, etc. being correlated to a clinical scale rating seriousness of specific alarm situations.

In the breathing apparatus 1, the processing unit may be configured to provide an alarm in the family view as a visual indication only. A remote alarm may be provided to clinical users via a network to which the apparatus 1 is connected. In addition, an acoustic alarm may be provided by the apparatus 1. The alarm sound may be different than a usual clinical alarm. Preferably, the acoustic alarm, if present, is based on a sound less alarming than in a clinical expert mode of the same breathing mode.

Figure 6:
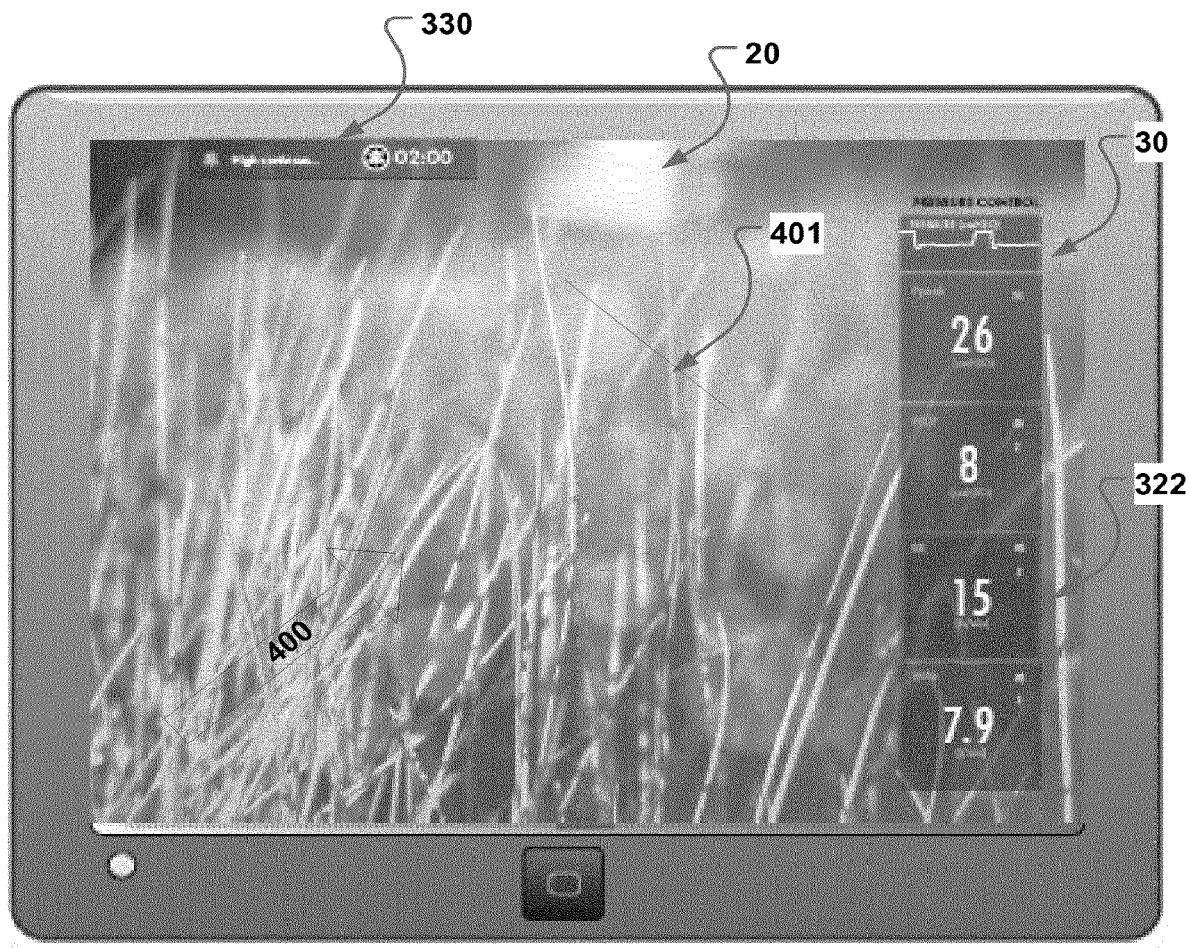

An alarm situation in family view 20 is now described with reference to FIG. 6. As an example, the operational parameter shown in metric display element 322 is supposed to have generated an alarm by exceeding a certain threshold during ventilation. The metric display element 322 is highlighted to draw attention to it. In the example, a frame with a solid color is generated around the metric display element 322. Moreover, the metric display element 322 is provided with an opaque background in a different color than the other metric display elements not causing an alarm. The color in the example is red.

A networked alarm may be added in the background to remotely draw the attention of clinical personnel to the alarm situation.

In addition, an alarm message window 330 may be displayed showing a text message related to the alarm. The alarm message window 330 may also include a timer if the alarm has been set to quiet by an operator. In case of screen 2 being a touch screen, the silent mode may be entered by touching the screen at a specific area of the screen dedicated for this purpose. The screen may be touched at this specific area, if present, to enter silent mode. The specific display area may be the metric display element related to the alarm. Touching the screen at other locations, or anywhere if the specific area for silencing an alarm is not provided, returns operation to the first operational mode, i.e. the second operational mode is left to a clinical mode. For returning to the second operational mode, e.g. when the cause of the alarm is taken care of and the alarm is reset, the operator has to re-enter the second operational mode as required by the breathing apparatus, such as described herein with reference to FIG. 8.

Alternatively, or in addition, a specific visual alarm indicator (not shown), external to the display, may be activated to draw attention to the alarm situation. The visual alarm indicator may be a specific light source, like a light emitting diode, or another lamp. The light source may illuminate an illumination element like a frame around the display. The light of the alarm may be differentiated between various degrees of severity of an alarm. For instance, the intensity of the visual indication may be increased with severity of an alarm on a predefined scale. Alternatively, or in addition, the color may be changed with increasing severity of the alarm. Alternatively, or in addition, the visual alarm may be chosen different in the first and second operational modes. Thus, a less stressful alarm indication may be provided when secondary users are present.

Figure 7:
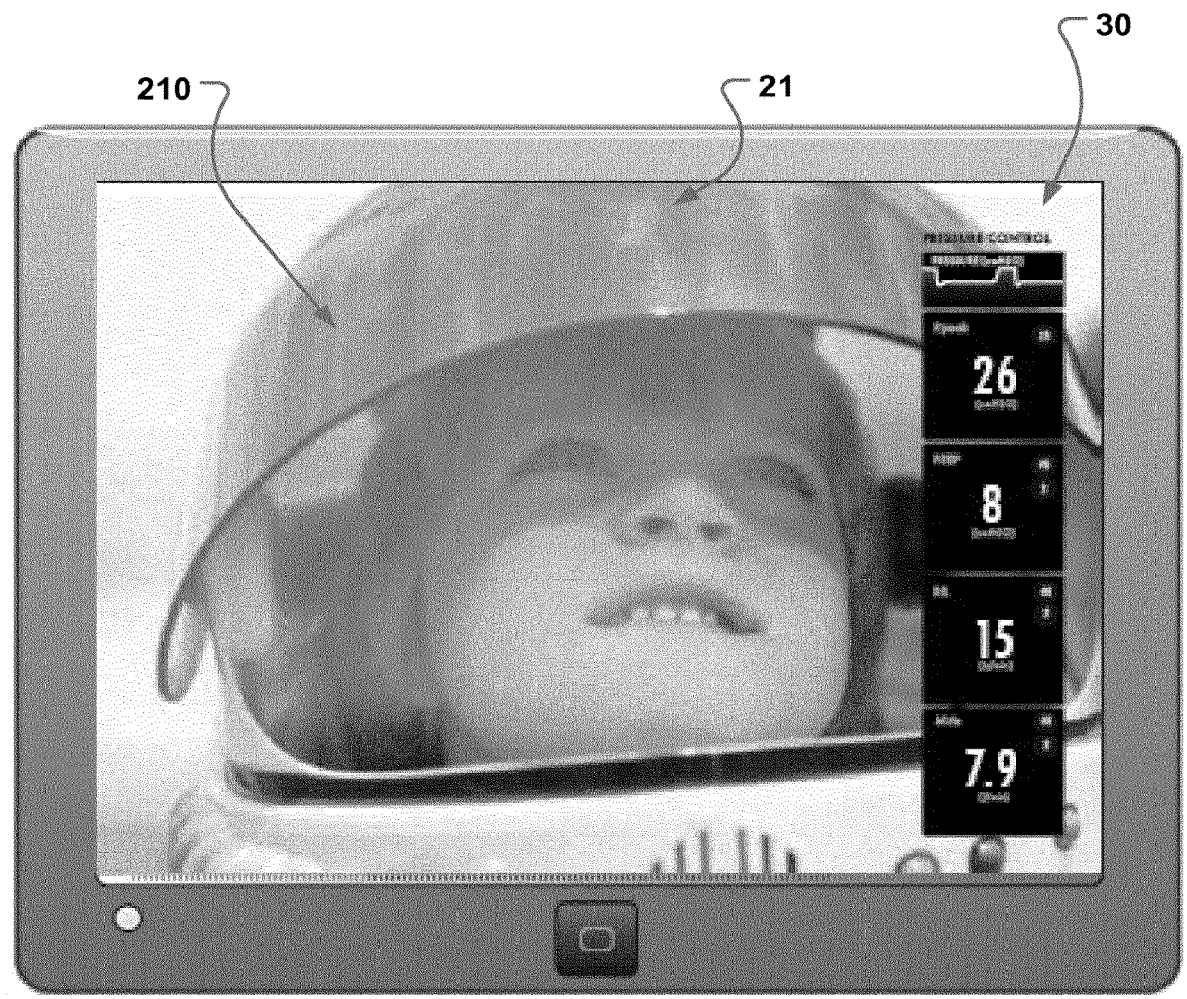

Another example of a family view is illustrated with reference to FIG. 7. The view 21 has a background image 200 is displayed on screen 2. In the example, the background image is a person, which might be an image of the ventilated patient. It should be noted that the image of the illustrated person in FIG. 7 is purely a non-limiting example of a background image. The image is chosen by the operator or user, and/or provided by the user, e.g. the secondary user. On a first display area 30 information data elements related to the current breathing mode 300 are displayed. The information data elements are shown with a black, non transparent background.

The interface 7 may be provided for connection of an external memory unit 6. The external memory unit 6 may have stored data for an image thereon, for access by the processing unit 5. Transfer of data may be done to the internal memory unit 3. The image data is thus accessible from the external memory unit 6 by the apparatus 1 and displayable on the display 2 as a background in a view. The external memory unit 6 may for instance be a USB memory unit, memory card with integrated WiFi, a memory unit in a personal communication device, like a cell phone, etc. The interface 7 may be one or more of a wired interface or a wireless interface. The interface 7 may of any technology suitable for transfer of data, like USB, memory card readers, docking stations for mobile telephones, WiFi, ZigBee, Bluetooth, etc.

The interface 7 may also be a network interface, so that background data is downloadable from the network. The network may be the Internet, so that background data is downloadable from the Internet. The external memory 6 may be located on a remote server (not shown).

Data, in particular background data elements, is thus transferable from the external memory 6 via the interface 7 the apparatus 1.

Any memory unit for a background data, like a background image is preferably kept separate from a memory having stored data for an operative system or function of the apparatus 1. The memory unit for a background data may be a protected memory range within a larger capacity memory unit. Any person may thus upload background data, like an image and/or sound to the apparatus in a safe way. The upload process may be controlled by an application software for this specific purpose, also called an app. The app may be provided for a execution on a personal communication device, such as a smart phone or similar mobile device, that can communicate with the breathing apparatus, e.g. via interface 7. The clinical function of ventilation is thus kept separate and cannot be influenced by the external background data accessibility. This provides for operational safety while operational flexibility of the apparatus 1 is increased.

Alternatively, or in addition, background data may be provided for a plurality of background images or the like. A background image in the second operational mode may thus comprise a plurality of subsequently displayable images. Thus a slide show may be provided as a background. A delay for switching between subsequent background images may be selectable or fixed.

Figure 8:

FIG. 8 is an illustration of a screen on display 2 for entering a second operational mode, here a family view with a preview thereof. The processing unit 5 may be configured to provide switching the apparatus from the first operational mode to the second operational mode upon acknowledgement of an operator only. Acknowledgement may be done by pressing an acknowledge button 62 on a touch screen. The processing unit 5 is preferably configured to control the display such that on a display area thereof a preview of the second operational mode is presented before the actual switching, i.e. activation of the second operational mode. The preview mode, such as shown in FIG. 8, may be entered by a Tap and Hold, and an Accept step on a touch screen.

The second operational mode may be left in a number of ways. One is that operation returns to the first operational mode. The processing unit may be configured to provide switching the apparatus 1 from the second operational mode to the first operational mode without user acknowledgement. For instance as by touching the display when the display is a touch sensitive display. One way is that the second operational mode is left immediately, preferably to the first operational mode, by an operator touching, e.g. tapping, anywhere on the display 2. Alternatively, an operator may touch the display at one or more defined sub areas of the display dedicated for the purpose of allowing quickly leaving the second operational mode. Alternatively, in addition, the apparatus 1 may leave the second operational mode automatically in certain predefined alarm scenarios.

Figure 9:
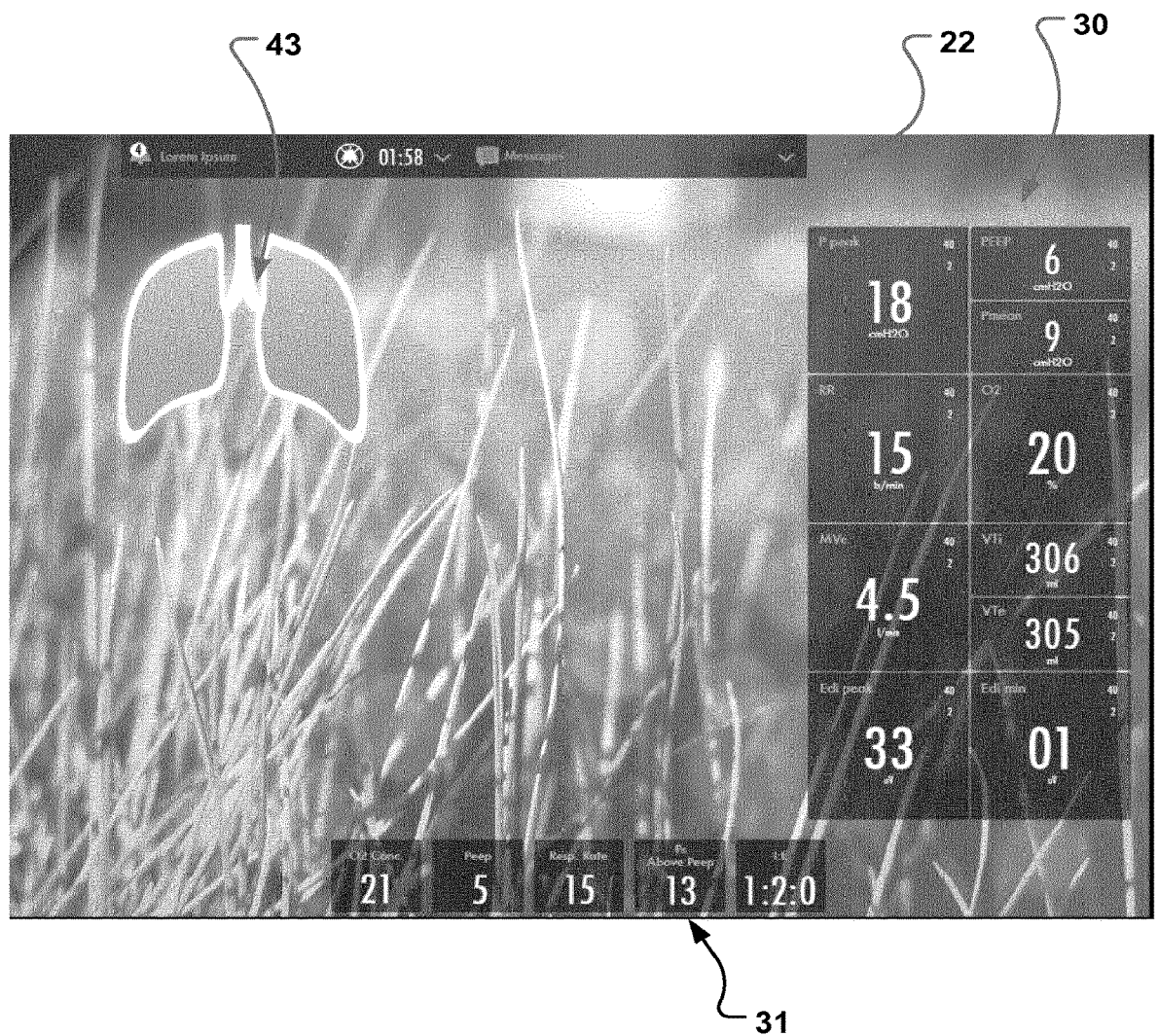

FIG. 9 is an example of another family view 22. The view 22 comprises on the first display area 30 more information data elements related to the current breathing mode 300 compared to the first family view illustrated in FIG. 4. In addition, the family view 22 comprises a visual clinical representation, here illustrated in an example as an animated pair of lungs 43. Moreover, the family view includes a second display area 31 that comprises further operational breathing parameters display elements, however in a smaller size than those in the first display area 30.

The visual clinical representation, which in this example is illustrated as a pair of lungs may be moving synchronized with the breathing pattern of the ventilated patient. The illustrated pair of lungs 43 is a specific non-limiting example for a visual clinical representation. Another example is for instance that the illustrated blades of grass move synchronized with the breathing pattern. A further example for a visual clinical representation is an image of one or more alveoli. Another example for a visual clinical representation is a balloon that is illustrated as moving in a inflating and deflating motion. Other objects on the screen may move synchronized with the breathing pattern in other examples, like illustrations of a patient whose chest moves up and down, etc. Several animations may be combined and performed simultaneously. A visual clinical representation may be associated with compliance, resistance, or other lung barometric parameters of a ventilated patient.

Figure 10:
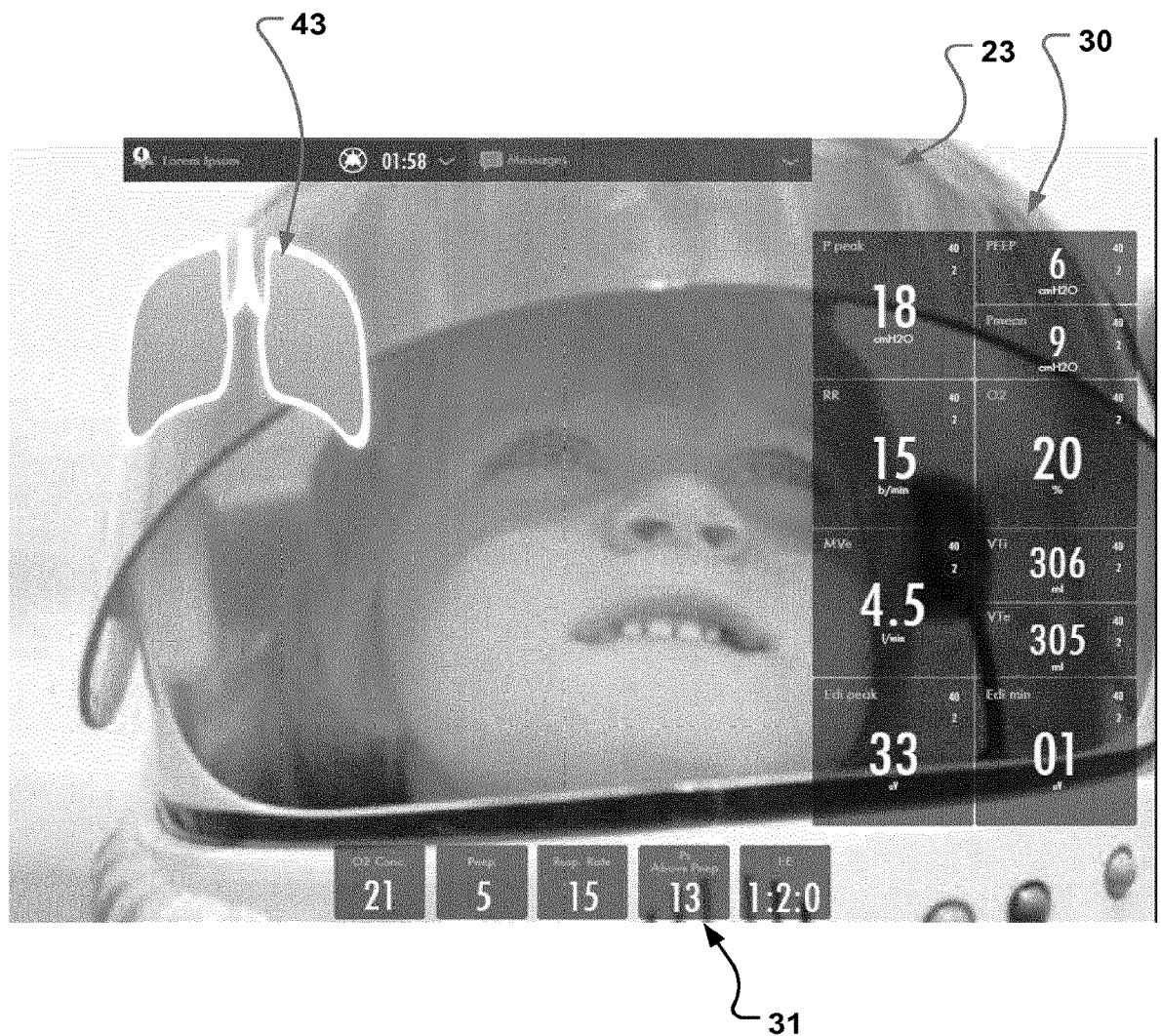

FIG. 10 is an alternative family view 23, similar to that shown in FIG. 9, with a user specific image in the background.

Figure 2:
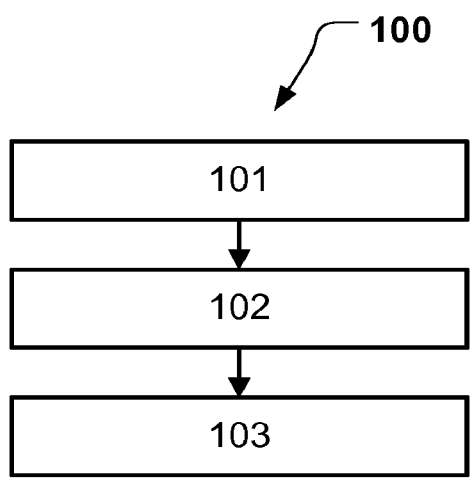
FIG. 2 is a flowchart illustrating a method.
Figure 3:
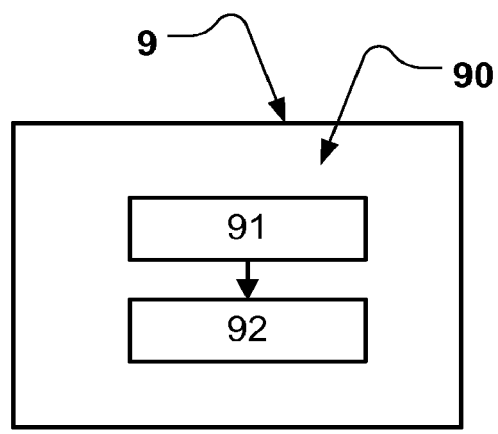
FIG. 3 is a schematic illustration of a computer-readable storage medium encoded with programming instructions.

According to another aspect of the disclosure, a method 100 is provided as illustrated in FIG. 2. The method 100 is a method of internally controlling a display 2 of a breathing apparatus 1. The method includes providing 101 a user selectable background for displaying 102 on at least a portion of the display 2, such as a background image, or a background color different than a factory default background color that is not selectable by a user. The background image is either selectable from at least one default image stored on an internal memory unit 3 of the breathing apparatus, or from an external memory unit 6 connectable to the breathing apparatus.

The method may further include switching 103 between a plurality of operational modes of the apparatus. The operational modes may include a first operational mode in which a first number of operational parameters is displayed on the display without the image as the background, and an alternative second operational mode in which a second number of operational parameters, preferably less than the first number, are displayed on the display and the background image is displayed as a background image on the display. The first and second operational modes are explained above.

The invention claimed is:

1. A breathing apparatus system comprising:
a breathing apparatus having a display, a memory unit, and a processing unit;
wherein the processing unit is in operative communication with the display and the memory unit, and the processing unit provides on at least a portion of the display a background that is stored on the memory unit; and
the processing unit provides a plurality of operational modes of the breathing apparatus, wherein the operational modes include
a first operational mode in which the processing unit causes the display to display a first number of operational parameters with a background color, wherein the first number of operational parameters comprise a plurality of metric elements; and
a second operational mode in which the background comprises a background image that includes an animated portion moving as a background object, and the processing unit causes the display to display in the second operational mode a second number of operational parameters and the background image that is displayed behind the second number of operational parameters, wherein the second number of operational parameters comprise a plurality of metric elements and the second number is less than the first number.

2. The system of claim 1, wherein the memory unit includes an internal memory unit that comprises at least one default background, wherein one background of a plurality of default backgrounds is selectable by a user.

3. The system of claim 1, wherein the display has a total display area, wherein the processing unit is configured to display a first number of metrics and/or time curves of operational parameters on substantially the entire display area in the first operational mode, and wherein the processing unit is configured to display at least a portion of the background image only on a display sub-area of the entire display area and/or opaquely or non-transparent behind a second number of the display metrics and/or time curves, less than the first number of metrics and/or time curves, in the second operational mode.

4. The system of claim 1, wherein the breathing apparatus is a ventilator and the animated portion illustrates an ongoing ventilation.

5. The system of claim 1, wherein the second operational mode is user selectable.

6. The system of claim 1, wherein the background is a user selectable background.

7. The system of claim 6, wherein the memory unit comprises an internal memory unit and an external memory unit, wherein the breathing apparatus comprises an interface for connection of the external memory unit having the image stored thereon, for access by the processing unit and/or transfer to the internal memory unit, wherein the background image from the external memory unit is accessible from the external memory unit by the breathing apparatus and displayable on the display as the user selectable background.

8. The system of claim 6, wherein the breathing apparatus has a plurality of operational modes, and wherein the user selectable background is different in different operational modes.

9. The system of claim 6, wherein the user selectable background is different for different patient categories selected from the group consisting of an adult product, a pediatric product, and a neonatal product.

10. The system of claim 1, wherein the processing unit is configured to display the background image opaquely behind at least a portion of the display where a foreground object, comprising operational parameter values, is displayed.

11. The system of claim 1, wherein the processing unit is configured to switch the breathing apparatus from the first operational mode to the second operational mode only upon acknowledgement of a user, and/or wherein the processing unit is configured to control the display so that on a display area thereof a preview of the second operational mode is presented before switching.

12. The system of claim 1, wherein the display is a touch sensitive display and the processing unit is configured to switch the breathing apparatus from the second operational mode to the first operational mode without user acknowledgement by touching the display.

13. The system of claim 1, wherein the processing unit is configured to provide an alarm in the second operational mode as a visual and acoustic indication, and to provide a remote alarm to at least one clinical user via a network to which the breathing apparatus is connected.

14. The system of claim 1, wherein the animated portion comprises a visual clinical representation wherein the visual clinical representation comprises an illustrated pair of lungs moving synchronized with the breathing pattern of the patient, or an image of one or more alveoli moving synchronized with the breathing pattern of the patient, or illustrated blades of grass moving synchronized with the breathing pattern of the patient, or an illustrated balloon inflating and deflating in synchronized movement with the breathing pattern of the patient.

15. The system of claim 1, wherein the animated portion includes a clinical animation and a stress reducing animation.

16. A method of internally controlling a display of a breathing apparatus, the method comprising the steps of:
displaying a background on at least a portion of the display, wherein the background comprises a background image, wherein the breathing apparatus is a ventilator or an anesthesia machine, and wherein the background image includes an animated image portion moving as a background object, wherein the animated image portion illustrates an ongoing ventilation; and
switching between a plurality of operational modes of the breathing apparatus, wherein the plurality of operational modes include a first operational mode in which a first number of operational parameters is displayed on the display without the background image, and a second operational mode in which a second number of operational parameters are displayed on the display and the background image is displayed in the background on the display behind the second number of operational parameters, wherein the first number of operational parameters comprise a plurality of metric elements and the second number of operational parameters comprise a plurality of metric elements, and wherein the second number is less than the first number.

17. A breathing apparatus system comprising:
a breathing apparatus having a display;
a memory unit configured to store an image; and
a processing unit in operative communication with the display and the memory unit, wherein the processing unit is configured to provide a plurality of operational modes of the breathing apparatus, wherein the operational modes include
a first operational mode in which the processing unit operates the display to display a clinical expert view that includes a first number of operational parameters on the display with a background color, and
a second operational mode in which the processing unit operates the display to display a family view that includes the image and a second number of operational parameters on the display, wherein the second number is less than the first number, and the image is displayed as a background image on the display behind the second number of operational parameters, and the image comprises a stress reducing animation.

18. The system of claim 17, wherein the stress reducing animation employs motion of an image element along a default trajectory in order to provide a stress reducing effect.

19. The system of claim 17, wherein the first number of operational parameters comprise a plurality of metric elements, or a plurality of time curves, or a combination of a plurality of metric elements and time curves.

20. The system of claim 17, wherein the second number of operational parameters comprise a plurality of metric elements, or a plurality of time curves, or a combination of a plurality of metric elements and time curves.

* * * * *